United States Patent
Frascotti et al.

(12)

(10) Patent No.: US 6,284,490 B1
(45) Date of Patent: Sep. 4, 2001

(54) **ASPOROGENOUS STRAIN OF *BACILLUS SUBTILIS* AND ITS USE AS A HOST FOR THE PREPARATION OF HETEROLOGOUS PRODUCTS**

(75) Inventors: Gianni Frascotti; Paola Cosmina; Guido Grandi, all of Milan (IT)

(73) Assignee: Eniricerche S.p.A., Milan (IT)

( * ) Notice: Subject to any disclaimer, the term of this patent is extended or adjusted under 35 U.S.C. 154(b) by 0 days.

(21) Appl. No.: 07/810,138

(22) Filed: Dec. 19, 1991

(30) Foreign Application Priority Data

Dec. 21, 1990 (IT) ................................ 22476 A/90

(51) Int. Cl.$^7$ ............................. C12N 15/09; C12N 1/21; C12N 1/20
(52) U.S. Cl. .................................. 435/69.4; 435/252.31; 435/252.5
(58) Field of Search ............................ 435/252.31, 252.1, 435/69.1, 71.2, 320.1, 172.3, 252.5, 69.4

(56) References Cited

U.S. PATENT DOCUMENTS

| | | | |
|---|---|---|---|
| 4,302,544 | * | 11/1981 | Young et al. .................. 435/252.31 |
| 4,450,235 | * | 5/1984 | Dean et al. .................... 435/252.31 |
| 4,450,236 | * | 5/1984 | Dean et al. .................... 435/252.31 |
| 4,465,773 | * | 8/1984 | Dean et al. .................... 435/252.31 |
| 5,015,574 | * | 5/1991 | Furatani et al. ................. 435/69.1 |
| 5,047,333 | * | 9/1991 | Grandi ............................. 435/68.1 |

FOREIGN PATENT DOCUMENTS

WO8904866 * 6/1989 (WO).

OTHER PUBLICATIONS

Sandman et al, Genetics, 117:603–617 (1987).*

* cited by examiner

*Primary Examiner*—James Ketter
*Assistant Examiner*—Lisa Gansheroff
(74) *Attorney, Agent, or Firm*—Sughrue, Mion, Zinn, Macpeak & Seas, PLLC

(57) ABSTRACT

The invention relates to a new asporogenous strain of *Bacillus subtilis* which has been deposited at the Centraalbureau Voor Schimmelcultures under the number CBS 432.90. This strain, which shows a frequency of reversion to the formation of spores of less than about $10^{-8}$ and good plasmid stability, is suitable as a host in a host-vector system for the preparation of heterologous products of interest.

7 Claims, 2 Drawing Sheets

ASPOROGENOUS STRAIN OF *BACILLUS SUBTILIS* AND ITS USE AS A HOST FOR THE PREPARATION OF HETEROLOGOUS PRODUCTS

The present invention relates to the asporogenous strain *Bacillus subtilis* SMS275 CMS 432.90 and its use as a host in a host-vector system for the preparation of heterologous products.

It is known in the art to prepare proteins and polypeptides by fermentation methods which use certain production systems, where this term means the combination of an expression vector containing the gene which codes for the protein or the polypeptide and the host which contains it.

Most recombinant products currently on the market are produced with the use of production systems which use *Escherichia coli*, CHO cells, or *Saccaromyces cerevisiae* as hosts.

However, these systems are not completely satisfactory and there is therefore a need in the art to provide other production systems for the preparation of heterologous products based, fundamentally, on the use of host organisms such as, for example, bacteria like Bacillus and Streptomyces or yeasts and fungi like *Kluyveromyces lactis* and *Yarrowia lipolytica* or insect cells.

From an industrial point of view, an ideal production system should enable the preparation of a recombinant product which can be purified easily and which has biological activity identical to that of the natural protein with high yields and at economically attractive costs.

Such a system should be constituted by:
1) a vector which contains strong regulation elements (promoter and terminator), of which many copies are present in the cells, and which is conserved within the cells in a stable manner so as to produce a high yield of the product of interest, and
2) a host which correctly carries out the instructions provided for the heterologous gene so as to enable the production of a product which is identical to the natural product, and which is suitable for culture on a commercial scale, that is, which is resistant, can multiply to high densities, is not very demanding as regards its need for nutritive elements, and is safe, that is, does not produce toxic contaminants.

At the moment there is considerable interest in the development of expression systems for the production of recombinant products in *Bacillus subtilis* (*B. subtilis*).

In fact *B.subtilis* is a particularly attractive microorganism from a biotechnological point of view because of its completely non-pathogenic nature, its ability to secrete the gene-expression product in the culture medium and, finally, because of the ease with which it can be grown on a large scale.

The use of *B.subtilis* as a host for the expression of heterologous proteins and polypeptides of interest to the pharmaceutical and food industries may thus be a determining factor for the approval of processes for the production of these products.

A partial contraindication with regard to the use of the micro-organism results, however, from its ability to give rise to the formation of spores under certain physiological growth conditions.

In fact spores, which are characterised by high resistance to chemical-physical agents have a high probability of survival under most normal environmental conditions.

The use of a recombinant strain of *B.subtilis* in a method of producing products of interest in the pharmaceutical and food fields may consequently encounter legal obstacles if it is not shown that there is a low probability of any spores generated being dispersed into the outside environment.

The formation of endospores in *B.subtilis* is a cell-differentiation process which takes place by means of sequential changes in the physiology of the cells and in their ultrastructure as a result of a response to conditions in which growth nutrients are restricted.

During sporulation which, on average, takes from 6 to 8 hours at 37° C., the cell passes through a series of well-defined morphological stages which terminate with the formation, within the sporangium, of an alternative cell form to the vegetative form, the endospore.

These stages, which are conventionally defined as stages (0–VII), require a series of substances which are coded by different genes, the spo genes.

The preparation of strains of *B.subtilis* which do not produce spores (asporogenous strains) by the mutation of a spo gene by chemical or physical agents or with the use of mutagenesis techniques in vitro is known in the art.

The mutants, which can no longer bring the formation of the spores to maturity, can in theory be used to prepare heterologous proteins.

Some of the mutants, however, have been found not to be completely satisfactory hosts for the development of systems for the asporogenous expression of *B.subtilis* because of the instability of the spo$^-$ phenotype, because of their inability to conserve the expression vector in a stable manner, and finally, because of the small number of copies of the vector present in the strain.

An asporogenous mutuant of *B. Subtilis* which overcomes the problems described above has now been isolated. This mutant, known as SMS275, has been deposited on Oct. 5, 1990 at the Centraalbureau Voor Schimmelcultures, Oosterstraal Postbus 273, NL-3740 AG Baarn Netherlands where it received the number CBS 432.90.

A subject of the present invention is therefore the asporogenous strain *Bacillus subtilis* SMS 275.

A further subject of the present invention is the use of the strain as a host in a host-vector system for the production of heterologus products.

Another subject of the present invention is a method for the preparation of a heterologous product of interest, including the transformation of the asporogenous strain *Bacillus subtilis* SMS 275 by an expression vector containing the gene which codes for the heterologous product, the growth of the transformed strain *Bacillus subtilis* SMS 275 in a suitable culture medium and, finally, the separation and purifcation of the gene-expression product thus produced.

In particular, the asporogenous strain *Bacillus subtilis* SMS 275 according to the present invention is characterised by the genetic markers spoII:D$^-$, leu (an inability to grow in minimal medium in the absence of leucine), pyrD1 (an inability to grow in minimal medium in the absence of uracil), apr$^-$ and npr$^-$ (the inability to produce serinic protease and neutral protease).

The strain can also conserve the spo$^-$ phenotype in a stable manner, actually reverting to the formation of spores with a frequency of less than about $10^{-8}$, and can conserve a large number of copies of a replicable expression vector in a stable manner.

The strategy used to construct the asporogenous strain according to the present invention consists of the mutation of a sporogenous strain of *B.subtilis* by a transposon and the isolation of the asporogenous mutants thus produced.

Transposons are elements of DNA which can be moved and inserted at different points in the genome, conferring new hereditary properties to the host strain. In fact, after insertion at points in the genome, as well as interrupting the sequence of a gene, which is manifested by a phenotypic mutation, transposons, which contain genes which code for resistance to antibiotics, confer to the host resistance to a particular antibiotic.

According to one embodiment of the present invention, the transposon TN917 (Tomich and Clewell, (1980), J. Bacteriol., 141: 1366–1574), which, amongst other things, codes for resistance to the antibiotic erythromycin (Em), is used.

Mutation by the insertion of a transposon can be carried out by conjugation or transformation according to known techniques.

In particular, the asporogenous strain according to the present invention was produced by transforming the wild type (sporogenous) strain *B.subtilis* SMS 118 with a plasmid which is not replicable in Bacillus and which contains the transposon TN917 and selecting the mutated strains on a medium supplemented with erythromycin.

In fact, in theory, only the clones in which the transposon TN917 has been integrated into the chromosomal DNA of the sporogenous strain can grow on this medium.

Plasmids suitable for the purpose may be, for example, pTV1TS, pTV32TS, or pTV51TS (Youngmann et al. "Regulation of Prokaryotic development" (ed.) I. Smith, R. A. Slepacky and P. Settlow, American Soc. for Microbiology, pages 65–87, 1989). Atlernatively, the transposon TN917 may be isolated from the plasmid pAD2 [Tomich and Clewell, (1980), J. Bacteriol., 141: 1366–1574] and introduced into a plasmid which is not replicable in *B.subtilis*.

The inability of the erythromycin-resistant clones to sporulate was tested both by analysis under an optical microscope and by direct display on sporulation medium where the colonies which could sporulate assumed a brown coloration after a few days, whilst the asporogenous colonies remained white and tended to lyse.

Some Em-resistant (Em$^r$) transformants analysed showed the spo$^-$ phenotype.

One of the spo$^-$ transformants, called SMS275, which contained the mutation in the spoII:D gene was further characterised to check the stability of the leu, pyrD1, apr$^-$ and npr$^-$ genotypes.

The analysis of the leu and pyrD1 markers was effected by growing the strain SMS275 on minimal medium in the absence and in the presence of leucine and uracil. The ability of the strain to grow only in the medium containing both the compounds confirmed the stability of the markers.

The analysis of the apr$^-$ and npr$^-$ markers was effected by plating the strain SMS275 on a maximal medium such as, for example VY or TBAB (DIFCO) containing casein at a concentration of 1%. The absence of haloes around the SMS275 colonies indicated the inability of the strain to produce the two proteases.

Finally, the stability of the spo$^-$ phenotype of the strain SMS275 was determined by treating the strain at high temperatures.

This test is based on the fact that strains which cannot generate spores (spo$^-$ phenotypes) show reduced resistance to short treatments at a high temperature.

Since the heat treatment destroys the cells but not the spores, the colonies which grow on plates will be those derived from any spores which were generated during the growth in the liquid medium and which were able to germinate when plated on maximal medium.

For this purpose, the strain SMS275 was grown in sporulation medium at 37° C. for about 24 hours and then subjected to heat treatment at 80° C. for about 10 minutes. Suitable dilutions of the culture were then plated on maximal medium containing kanamycin and chloramphenicol and the viable cells (CFU) were then counted.

An analysis of the data showed that the frequency with which the strain SMS275 reverted to the spo$^+$ phenotype was less than $1\times10^{-8}$.

The strain *B.subtilis* SMS275 thus seems particularly suitable for use as a host in a host-vector system for the production of heterologous products of interest.

The method according to the present invention consists, for example, of transforming the asporogenous strain with a replicable expression vector containing the gene which codes for the heterologous product of interest, growing the asporogenous strain thus transformed under suitable conditions and, finally, isolating and purifying the gene-expression product obtained.

Suitable vectors may be selected from plasmids which replicate in *B.subtilis* and are available from laboratories and collection centres.

The transformation of the *B.subtilis* SMS275 cells by these vectors is carried out with the use of one of the conventional techniques.

The asporogenous strain *B.subtilis* SMS275 may be useful as a host for the expression of genes which code for a prokaryotic polypeptide such as, for example an enzyme such as alpha-amylase, beta-amylase, etc., or for a eukaryotic polypeptide such as interleukin, interferons, human growth hormone, or precursors thereof.

According to one embodiment of the present invention, the strain *B.subtilis* SMS275 was transformed by the plasmid pSM274 which contains the DNA sequence which codes for the precursor of human growth hormone, as described in U.S. Pat. No. 5,047,333.

The transformed strain was then grown to an optical density of about 3–4 determined at a wavelength of 600 nm in a culture medium containing sources of carbon, nitrogenous sources and mineral salts.

The stability of the plasmid and the ability of the strain SMS275 (pSM274) to produce the precursor of hGH was then determined.

The results confirmed the stability of the plasmid pSM274, a large number of copies of which were present in the cells (FIG. 1A).

Moreover, electrophoretic analysis of the total soluble proteins extracted from the strain showed the presence of a band corresponding to the precursor of human growth hormone.

The viability of the strain *B.subtilis* SMS275 (pSM274) was also evaluated by the determination of the number of viable cells per ml (CFU/ml) in a culture kept for 6 months in glycerol.

The results obtained showed that the viability of the cells was good in the conditions under which they were kept and that the spo$^-$ phenotype was stable.

The asporogenous strain *B. Subtilis* SMS275 containing the plasmid pSM274 was deposited at the Centraalbureau Voor Schimmelcultures, Oosterstraal Postbus 273, NL-3740 AG Baam Netherlands on Oct. 5, 1990 where it received the number CBS 433.90.

The comparison example 4 describes the transformation of *B.subtilis* spo$^-$ strains other than SMS275 by the plasmid pSM274.

When analysed for stability and the number of pairs of the plasmid and for the stability of the spo$^-$ phenotype, these strains gave the following results:

in the strain SMS268 with the spo0F mutation, the plasmid pSM274 was structurally unstable;

in the strain SMS270 with the spoIIA1 mutation, fewer copies of the plasmid pSM274 were present than with the wild type strain SMS118;

in the strain SMS272 with the spoIIF96 mutation, the plasmid was stable and the number of copies was comparable to that with the wild type strain SMS118. Based on an estimate carried out by microscope observation, however, this strain tends to reacquire the positive sporulation phenotype with a fairly high frequency.

Moreover, the strain SMS272 shows lower viability than the strain SMS275 (pSM274) when kept, for example, in glycerol.

In fact, after the addition of glycerol, the number of viable cells/ml of culture was $3.7 \times 10^7$ CFU/ml; after 7 days, this value was reduced to 73%, after 19 days to 68%, and after 40 days to about 54%.

For these reasons, the strain SMS272 is not suitable for use in an industrial fermentation process.

Figure 1A:
FIGS. 1A and 1B show.

Electrophoretic analysis on agarose gel of the DNA of the plasmid pSM274.

A. 1) pSM274 control, not digested;
2) pSM274 control digested with Eco RI and Hind III;
3) plasmid DNA, not digested, extracted from the strain SMS 275 (pSM274);
4) plasmid DNA extracted from the strain SMS275 (pSM274) and digested with Eco RI and Hind III;
5) molecular-weight standards.

B. 1–4) plasmid DNA extracted from 2 clones of the strain spoIID SMS275 (pSM274) in which, in 1 and 3, the DNA was not digested and, in 2 and 4, the DNA was digested with Eco RI and Hind III;
5–8) plasmid DNA extracted from 2 clones of the strain spoIIA1 SMS270 (pSM274) in which, in 5 and 7, the DNA was not digested and, in 6 and 8, the DNA was digested with Eco RI and Hind III;
9) molecular-weight standards;
10–13) plasmid DNA extracted from 2 clones of the strain spoIIF96 SMS272 (pSM274) in which, in 10 and 12, the DNA was not digested and, in 11 and 13, the DNA was digested with Eco RI and Hind III;
14 and 15) plasmid DNA extracted from 1 clone of the strain spo0F SMS228 (pSM274) in which, in 14, the DNA was not digested and, in 15, the DNA was digested with Eco RI and Hind III;

FIG. 2 shows:

Electrophoretic analysis on 12.5% sodium dodecyl-polyacrylamide gel (SDS-PAGE) of the proteins extracted from the strain SMS275 (pSM274).

lane A) standard (partially purified hGH precursor);

lane B) proteins extracted from the strain SMS275 transformed by the control plasmid pSM214 which does not contain the sequence which codes for the hGH precursor.

lanes C–F) proteins extracted from 4 clones of the strain SMS275 transformed by the plasmid pSM274.

The following examples are illustrative of the invention but are non-limiting.

EXAMPLE 1

Construction of the asporogenous strain B.subtilis SMS275

The plasmid DNA pTV5TS containing the transposon Tn917 (1 µg) was used to transform competent B.subtilis SMS118 cells by the method described by Contente and Dubnau (Mol. Genetics., (1979), 167: 251–258).

The transformants were then selected by plating the cells on 20 ml of VY maximal medium (veal infusion) (veal infusion broth (DIFCO) 25 g/l, yeast extract 5 g/l and agar (DIFCO) 20 g/l) and pouring onto the plates 5 ml of soft agar containing 125 µg/ml of erythromycin and incubating the plates at 37° C. for another 18 hours.

The erythromycin-resistant (Em$^r$) transformants, that is, those in which a homologous recombination had taken place at the chromosome level, were tested for their inability to generate spores.

For this purpose, the Em$^r$ colonies were transferred onto plates of Schaeffer sporulation medium having the following composition:

| | |
|---|---|
| Nutrient broth (DIFCO) | 8.0 g/l |
| KCl | 1.0 g/l |
| MgSO$_4$ | $1.25 \times 10^{-1}$ g/l |
| agar (DIFCO) | 16.0 g/l |
| MnCl$_2 \cdot$ 4 H$_2$O | $1.98 \times 10^{-3}$ g/l |
| FeSO$_4 \cdot$ 7 H$_2$O | $2.78 \times 10^{-4}$ g/l |
| Na$_2$SO$_4$ | $1.42 \times 10^{-1}$ g/l |
| H$_2$O | 1.0 liter |
| pH 7.0, and grown at 37° C. | |

After several days the formation of spores was determined both by observation under an optical microscope and by following the morphological alteration of the colonies.

The colonies which gave rise to spores in fact assumed a typical brown coloration whilst the asporogenous colonies remained clear and tended to lyse.

The results obtained as described above enabled some Em$^r$ transformants with the asporogenous phenotype (spo$^-$) to be isolated.

One of these transformants, containing a mutation in the spoII:D gene was identified by the symbols SMS275.

EXAMPLE 2

Characterisation of the Strain SMS275

The strain SMS275 was further characterised to check the stability of the genetic markers apr$^-$, npr$^-$, leu, pyrD1 and spo$^-$.

In particular, tests were carried out to check (i) the low protease activity in the growth medium of the strain (indicating that the serinic protease (apr) and neutral protease (npr) genes were inactivated, (ii) the inability of the strain to grow on minimal medium in the absence of leucine and uracil and (iii) its inability to sporulate.

The protease activity was determined by plating the strain SMS275 on VY maximal medium containing 1% of casein (Toma et al/. (1986), J. Bacteriol., 147:740–743). The absence of the characteristic hydrolysis halo around the colonies due to the action of serinic and neutral protease indicated that the two enzymes had not been secreted.

None of the colonies isolated from the strain SMS275 had hydrolysis haloes.

As regards the nutritional requirements for leucine (leu) and uracil (pyrD1), however, the control experiments were carried out by plating the strain on minimal medium having the composition described by P. Youngman (1986) in "Plasmids: a practical approach" K. G. Hardy (ed.), IRL Press, 79–103) without growth factors, in minimal medium containing only leu (50 µg/ml), in minimal medium containing only uracil (50 µg/ml), and in minimal medium containing both the products.

Growth was observed only on the medium containing both the nutritional factors thus confirming the stability of the genetic markers leu and pyrD1.

Finally, the quantity of any spores generated in relation to the total quantity of cells was determined and, at the same time, the stability of the spo⁻ phenotype in the absence of the selective pressure imposed by erythromycin was checked.

The analysis was based on the fact that strains which cannot generate spores show less resistance to short treatments at a high temperature.

Two 100 ml flasks each containing 10 ml of Schaeffer liquid sporulation medium were inoculated with the strain SMS275 and with the sporogenous strain SMS181 (the control), respectively, and incubated first at 37° C. for 24 hours and then at 80° C. for 10 minutes.

Aliquots of the cultures were then suitably diluted and 0.1 ml of each dilution was plated on VY maximal medium supplemented with the antibiotics. After growth at ambient temperature, the viable cells (CFU) were counted before and after treatment at 80° C.

Since the heat treatment destroys the cells but not the spores, the colonies grown on the plates were those which were derived from any spores which were generated during the growth in the liquid medium at 37° C. and were able to germinate when plated on the maximal medium.

Table I shows the results of the experiment expressed as CFU/ml.

TABLE I

| Dilution | SMS118 − | SMS118 + | SMS275 − | SMS275 + |
|---|---|---|---|---|
| t.q. | >$10^4$ | >$10^4$ | >$10^4$ | 0 |
| $10^{-2}$ | >$10^4$ | 141 | >$10^4$ | 0 |
| $10^{-4}$ | >$10^4$ | 2 | >$10^4$ | 0 |
| $10^{-6}$ | 19 | 0 | 10 | 0 |

The values given in the table represent mean values for three determinations.

t.q.: culture not diluted (0.1 ml);
−: before heat treatment
+: after heat treatment It can be seen from an analysis of the data that:

i) the number of cells present in the cultures of the strains SMS118 and SMS275 grown at 37° C. were $1.9 \times 10^8$ CFU/ml and $1 \times 10^8$ CFU/ml, respectively;

(ii) the frequency with which the strain SMS275 reverted to the spo+ phenotype was less than $1 \times 10^{-8}$ and the ratio between the percentages of SMS275 and of SMS118 surviving the heat treatment was less than 0.001%;

(iii) the quantity of spores which had been formed after 24 hours at 37° C. and which were able to germinate on maximal medium was $1.4 \times 10^5$ for the sporogenous strain SMS118 and 0 for the asporogenous strain SMS275.

Since the culture in a liquid medium at 37° C. was carried out in the absence of erythromycin, the complete absence of SMS275 colonies after heat treatment at 80° C. indicated that the spo⁻ characteristic acquired by the strain SMS275 was very stable.

In fact the cells, which might have lost the transposon, nevertheless retained the asporogenous phenotype.

EXAMPLE 3

Transformation of the Strain SMS275 by the Plasmid pSM274

Competent B.subtilis SMS275 cells were transformed by the plasmid pSM274 (10 nanograms (ng)) and the transformants were then selected on plates of VY maximal medium containing 5 µg/ml of kanamycin and 5 µg/ml of chloramphenicol at 37° C. for 18 hours.

An aliquot of the plasmid DNA isolated from one of the resistant clones by the rapid extraction method described in "Recombinant DNA Techniques: an introduction" [(Eds) Rodriguez and Tait, (1983), Addison-Wesley Publishing Company, 164] was digested with the restriction enzymes Eco RI and Hind III (BRL) according to the suppliers' instructions.

2 µl of the digested plasmid DNA and 2 µl of the same DNA which had not been digested were then loaded onto 0.8% agarose gel, as were the plasmid pSM274 (the control) (2 µl), treated with the same enzymes and untreated, and some molecular-weight standards.

The results given in FIG. 1A show that the plasmid pSM274 isolated from the B.subtilis SMS275 clone and digested with the restriction enzymes showed the expected migration speed and a digestion pattern in accordance with that of pSM274.

In fact, two bands corresponding to two fragments with lengths of 6700 bp and 800 bp which correspond, respectively, to the plasmid vector and to the insert which codes for the precursor of human growth hormone were resolved, after decoloration, with ethidium bromide.

Figure 2:
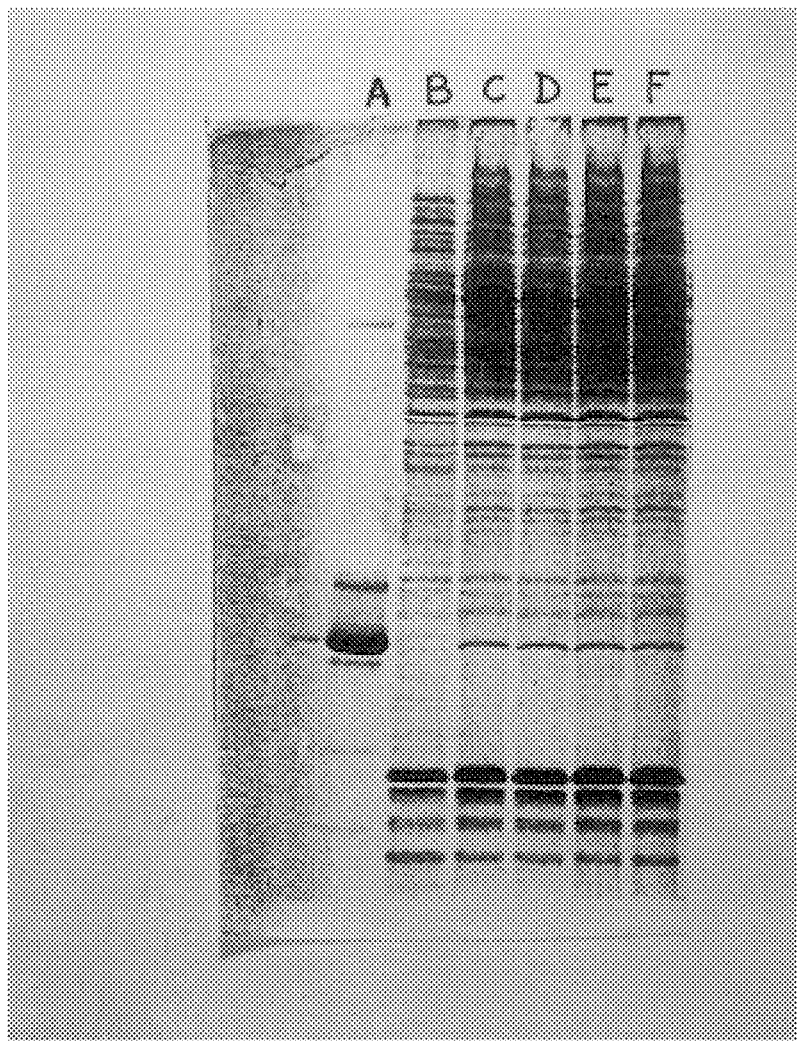

The ability of the strain B.subtilis SMS275 (pSM274) to produce the precursor of hGH was checked by growing the strain in 10 ml of VY medium at 37° C. for 18 hours and then analysing the total soluble proteins extracted from the lysed cells by electrophoresis on 12.5% SDS-PAGE and dying with Coomassie Blue. The presence of the band corresponding to the precursor of human growth hormone in the proteinaceous extract can be seen in FIG. 2.

EXAMPLE 4 (comparison)

Transformation of Asporogenous Strains Containing the spoIIF96, spoIIA1 and spo0F Mutations The asporogenous strains B.subtilis SMS268, SMS270 and SMS272 containing the spoIIF96, spoIIA1 and spo0F mutations, respectively, were transformed by the plasmid pSM274 and then examined to check the stability of the plasmid, the number of copies of the plasmid present, and the stability of the spo⁻ phenotype.

Figure 1B:
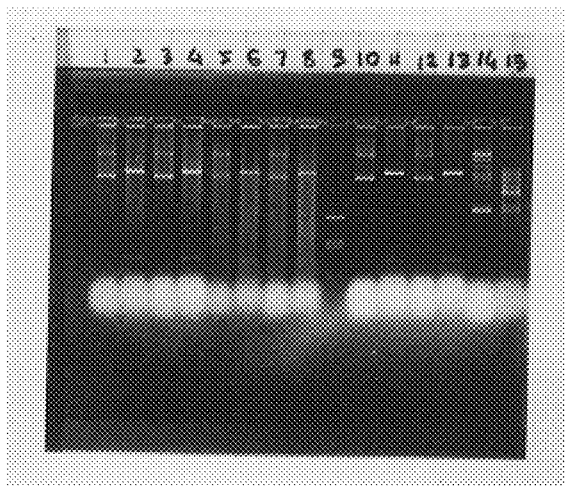

As can be seen from FIG. 1B, in the strain with the spo0F mutations, the plasmid pSM274 seemed unstable, whilst in the strain with the spoIIA1 mutation, a smaller number of copies of the plasmid was present than in the strain SMS118.

The strain spoIIF96, on the other hand, conserved the plasmid in a stable manner and with a number copies comparable to that with the strain SMS118.

When tested to check the stability of the spo⁻ phenotype, however, this strain showed a tendency to reacquire the positive sporulation phenotype with a fairly high frequency, based on an estimate carried out by microscopic observation.

EXAMPLE 5

Analysis of the Viability of the Asporogenous Strains SMS275 and SMS272

In order to check the viability of the strain SMS275, four cell banks were prepared in glycerol.

In practice, two 100 ml precultures of the strain SMS275 (pSM274) and of the strain SMS272 (pSM274) (control) were prepared in TYM medium with the following formulation:

| | |
|---|---|
| tryptone | 13 g/l |
| yeast extract | 3 g/l |
| maltose | 40 g/l |
| kanamycin | 5 mg/l |
| chloramphenicol | 5 mg/l |

The flasks were stirred at 220 rpm and incubated at 37° C. for 24 hours.

Two 2 l fermenters each containing 1 liter of TYM medium were then inoculated, each with 100 ml of one of the precultures (initial optical density (O.D.) 0.190 at 660 nm).

The fermentation was carried out at 800 rpm, pH 7.0 with the air being changed at 0.5 v/v/minute.

The cells were recovered by centrifuging the culture medium after fermentation for 15 hours to an O.D. of 3.0.

2ml samples were then supplemented with glycerol to a final concentration of 15% and kept at −80° C.

6 months after the date of preparation, the quantity of viable cells (colony-forming units—CFU) in the samples in glycerol was determined. The test consisted of diluting aliquots of the samples in glycerol with a culture medium and immediately plating 0.1 ml of the dilutions on TBAB maximal growth medium (DIFCO) with agar, with and without the anitbiotics kanamycin and chloramphenicol.

For SMS275 (pSM274), the number of viable cells per ml of the sample in glycerol was $2.4 \times 10^8$ CFU/ml the analysis being carried out both in the presence and in the absence of the antibiotics kanamycin and chloramphenicol.

These results indicate good stability and viability of the SMS275 cells under the conservation conditions used.

The CFU values obtained for SMS272 (pSM274), however, showed low viability.

In fact, after the addition of glycerol, $3.7 \times 10^7$ CFU/ml were measured. After 7 days this value fell to 73%, after 19 days to 68%, and after 40 days, to about 54%.

The cultures of the strain SMS274 (pSM274), analysed as described in Examples 2 and 3, also showed that the plasmid was stable and the sequence of the gene which codes for the precursor of hGH was intact.

We claim:

1. A biologically pure culture of asporogenous strain *Bacillus subtilis* SMS275, suitable for use as a host component in a host-vector system, characterized in that said strain has a frequency of reversion to spore formers of less than $10^{-8}$, plasmid stability, genetic markers leu, pyrD1, apr⁻, npr⁻ and spoII:D⁻, and is deposited as CBS 432.90.

2. The asporogenous strain *Bacillus subtilis* SMS275 according to claim 1, wherein said strain is transformed with a plasmid vector containing a gene coding for a heterologous polypeptide or protein or a precursor thereof and said plasmid vector is able to express said gene in said *Bacillus subtilis* SMS275.

3. The asporogenous strain *Bacillus subtilis* SMS275 according to claim 2, wherein said plasmid vector contains a gene coding for a precursor of human growth hormone.

4. The asporogenous strain *Bacillus subtilis* SMS275 according to claim 3, wherein said plasmid vector is pSM274 (CBS 75288).

5. The asporogenous strain *Bacillus subtilis* SMS275 (pSM274) according to claim 4, deposited as CBS 433.90.

6. A process for the production of a heterologous polypeptide or protein or a precursor thereof, comprising the steps of:

a) transforming an asporogenous strain *Bacillus subtilis* SMS275 with a plasmid vector containing a gene coding for a heterologous polypeptide or protein or a precursor thereof,
      wherein said asporogenous strain *Bacillus subtilis* SMS275 is characterized in that it has a frequency of reversion to spore formers of less than $10^{-8}$, plasmid stability, genetic markers leu, pyrD1, apr⁻, npr⁻ and spoII:D⁻, and is deposited as CBS 432.90;

b) culturing the transformed asporogenous strain *Bacillus subtilis* of step (a) in a suitable culture medium containing a carbon source, a nitrogen source, mineral salts, leucine and uracil; and (c) recovering said heterologous polypeptide or protein or a precursor thereof.

7. The process according to claim 6, wherein the heterologous polypeptide is a precursor of human growth hormone and the transformed asporogenous strain *Bacillus subtilis* of step b) is *Bacillus subtilis* SMS275 (pSM274) CBS 433.90.

* * * * *

UNITED STATES PATENT AND TRADEMARK OFFICE
CERTIFICATE OF CORRECTION

PATENT NO.    : 6,284,490 B1
DATED         : September 4, 2001
INVENTOR(S)   : Gianni Frascotti et al It is certified that error appears in the above-identified patent and that said Letters Patent is hereby corrected as shown below:

<u>Title page,</u>
Add in line [73]:
PHARMACIA AB, Stockholm, Sweden

Signed and Sealed this

Fifth Day of February, 2002

Attest:

JAMES E. ROGAN
*Attesting Officer*     *Director of the United States Patent and Trademark Office*